(12) United States Patent
Murata

(10) Patent No.: US 10,016,245 B2
(45) Date of Patent: Jul. 10, 2018

(54) JOINT MECHANISM AND MEDICAL EQUIPMENT

(71) Applicant: OLYMPUS CORPORATION, Tokyo (JP)

(72) Inventor: Takeshi Murata, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 189 days.

(21) Appl. No.: 15/002,600

(22) Filed: Jan. 21, 2016

(65) Prior Publication Data

US 2016/0135907 A1  May 19, 2016

Related U.S. Application Data

(63) Continuation of application No. PCT/JP2014/066780, filed on Jun. 25, 2014.

(30) Foreign Application Priority Data

Jul. 25, 2013  (JP) ................................. 2013-154469

(51) Int. Cl.
    *G05G 1/00* (2006.01)
    *A61B 34/30* (2016.01)
    (Continued)

(52) U.S. Cl.
    CPC .............. *A61B 34/30* (2016.02); *F15B 15/06* (2013.01); *F16H 21/36* (2013.01); *F16H 21/48* (2013.01);
    (Continued)

(58) Field of Classification Search
    CPC ...... F16H 21/36; F16H 37/124; F16H 37/126; F16H 21/14; F16H 21/48; F16H 21/54; F15B 15/06
    See application file for complete search history.

(56) References Cited

U.S. PATENT DOCUMENTS 229,295 A * 6/1880 Underwood ........... A01C 19/00
                                                  74/67
238,839 A * 3/1881 Bond, Jr. ................ A01C 19/00
                                                  112/284
(Continued)

FOREIGN PATENT DOCUMENTS

EP      2 623 272 A1    8/2013
JP      2008-307310 A   12/2008
(Continued)

OTHER PUBLICATIONS

International Search Report dated Sep. 22, 2014 issued in PCT/JP2014/066780.
(Continued)

*Primary Examiner* — William J Cook
(74) *Attorney, Agent, or Firm* — Scully, Scott, Murphy & Presser, P.C.

(57) ABSTRACT

Provided is a joint mechanism including two spur gears and; a support member that supports the two spur gears and so as to be rotatable about two joint shafts and that are disposed in a skew-lines positional relationship with a space between each other; and a rotational-force transmitting mechanism that transmits a rotational force between the spur gears and, wherein the rotational-force transmitting mechanism is provided with a transmission member formed of a rigid piece that is supported so as to be movable only in a direction parallel to a line of intersection between planes and that are respectively orthogonal to the two joint shafts and cam mechanisms or linkage mechanisms that are disposed between the transmission member and the two spur gears and, respectively, and that convert rotational motions of the spur gears and to a linear motion of the transmission member.

4 Claims, 6 Drawing Sheets

(51) Int. Cl.
　　*F16H 21/48*　　　(2006.01)
　　*F15B 15/06*　　　(2006.01)
　　*F16H 21/54*　　　(2006.01)
　　*F16H 21/36*　　　(2006.01)
　　*F16H 37/12*　　　(2006.01)
　　*F16H 21/14*　　　(2006.01)

(52) U.S. Cl.
　　CPC ........... *F16H 21/54* (2013.01); *F16H 37/124* (2013.01); *F16H 37/126* (2013.01); *A61B 2034/305* (2016.02); *F16H 21/14* (2013.01)

(56) References Cited

U.S. PATENT DOCUMENTS 248,775 A * 10/1881 Merriman .............. A01C 19/00
　　　　　　　　　　　　　　　　　　　　　　74/50
2004/0199147 A1　10/2004　Nishizawa et al.
2008/0310945 A1　12/2008　Tsujita et al.
2009/0100948 A1* 4/2009　Ushiku ................ B60N 2/0232
　　　　　　　　　　　　　　　　　　　　　　74/49
2012/0239058 A1　9/2012　Namiki

FOREIGN PATENT DOCUMENTS

JP　　2012-91310 A　　5/2012
JP　　2012-192004 A　　10/2012

OTHER PUBLICATIONS

Extended Supplementary European Search Report dated Feb. 16, 2017 in European Patent Application No. 14 83 0003.1.

* cited by examiner

JOINT MECHANISM AND MEDICAL EQUIPMENT

CROSS-REFERENCE TO RELATED APPLICATIONS

This is a continuation of International Application PCT/JP2014/066780, with an international filing date of Jun. 25, 2014, which is hereby incorporated by reference herein in its entirety. This application claims the benefit of Japanese Patent Application No. 2013-154469, the content of which is incorporated herein by reference.

TECHNICAL FIELD

The present invention relates to a joint mechanism and medical equipment.

BACKGROUND ART

There are known joint mechanisms provided with a shaft portion; two gears that are provided so as to be rotatable about rotation shafts disposed at both ends of the shaft portion in a skew-lines positional relationship with each other; and spring linkages coupled with the individual gears via coupling pins that are parallel to the rotation shafts of the gears (for example, see Patent Literature 1). With the joint mechanism according to Patent Literature 1, in association with the rotational motion of a first gear, a spring linkage transmits the rotational force to a second gear while elastically being deformed in an axial cross-sectional direction of the shaft portion, thus rotating the second gear.

With the joint mechanism according to Patent Literature 1, because the linkage that transmits the rotational force of the gear to another gear having a separate rotation shaft is formed of a spring member, the linkage cannot endure when a high load is exerted on the joint mechanism, and thus, the linkage is elastically deformed, making it impossible to transmit the rotational force.

The present invention has been conceived in light of the above-described circumstances, and an object thereof is to provide a joint mechanism with which it is possible to transmit a high-load rotational force between two rotation members disposed so as to be rotatable about axes that are disposed in a skew-lines positional relationship, and to provide medical equipment including such a joint mechanism.

CITATION LIST

Patent Literature

{PTL 1} Japanese Unexamined Patent Application, Publication No. 2012-91310

SUMMARY OF INVENTION

Solution to Problem

An aspect of the present invention is a joint mechanism including two rotation members; a support member that supports the two rotation members so as to be rotatable about two joint shafts that are disposed in a skew-lines positional relationship with a space between each other; and a rotational-force transmitting mechanism that transmits a rotational force between the rotation members, wherein the rotational-force transmitting mechanism is provided with a transmission member formed of a rigid piece that is supported so as to be movable only in a direction parallel to a line of intersection between planes that are respectively orthogonal to the two joint shafts and cam mechanisms or linkage mechanisms that are disposed between the transmission member and the two rotation members, respectively, and that convert rotational motions of the rotation members to a linear motion of the transmission member.

DESCRIPTION OF EMBODIMENT

A joint mechanism 1 and medical equipment 2 according to an embodiment of the present invention will be described below with reference to the drawings.

Figure 1:
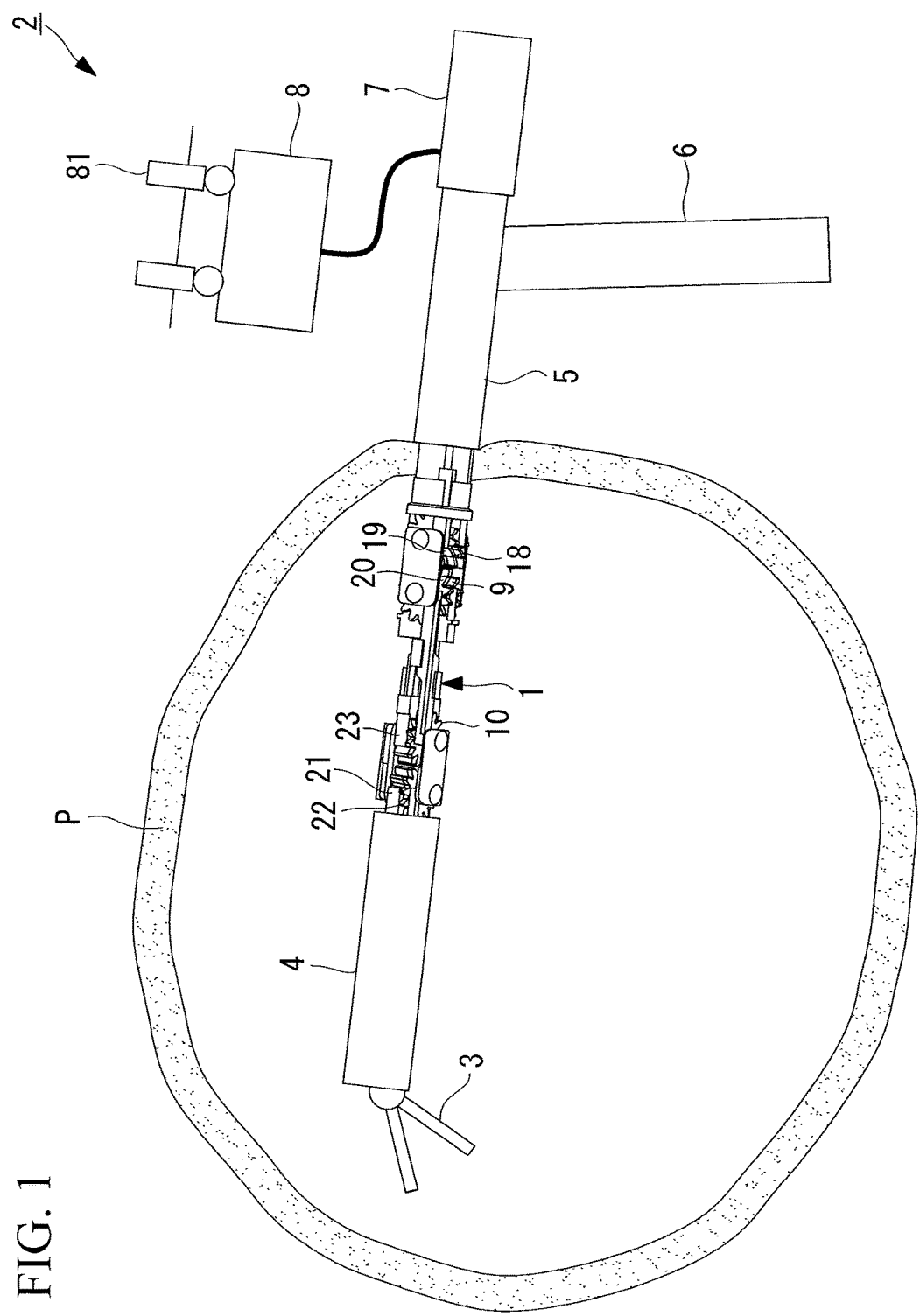
FIG. 1 is a schematic view showing medical equipment according to an embodiment of the present invention.

As shown in FIG. 1, the medical equipment 2 according to this embodiment is a treatment tool that is provided with, at the distal end thereof, an end effector 3, such as forceps, that is inserted into the body of a patient P to treat an affected site. The medical equipment 2 is provided with two linkage members 4 and 5 and the joint mechanism 1 according to this embodiment that couples the linkage members 4 and 5. The linkage member 4, which is disposed on the distal-end side, supports the end effector 3 at the distal end thereof. The linkage member 5, which is disposed on the base-end side, is supported at the top end of a support pillar 6 in a pivotable manner. In FIG. 1, reference sign 7 is a drive unit 7 that drives the linkage member 4, and reference sign 8 is a control portion 8 having a manipulation portion 81 that controls the drive unit 7.

Figure 2:
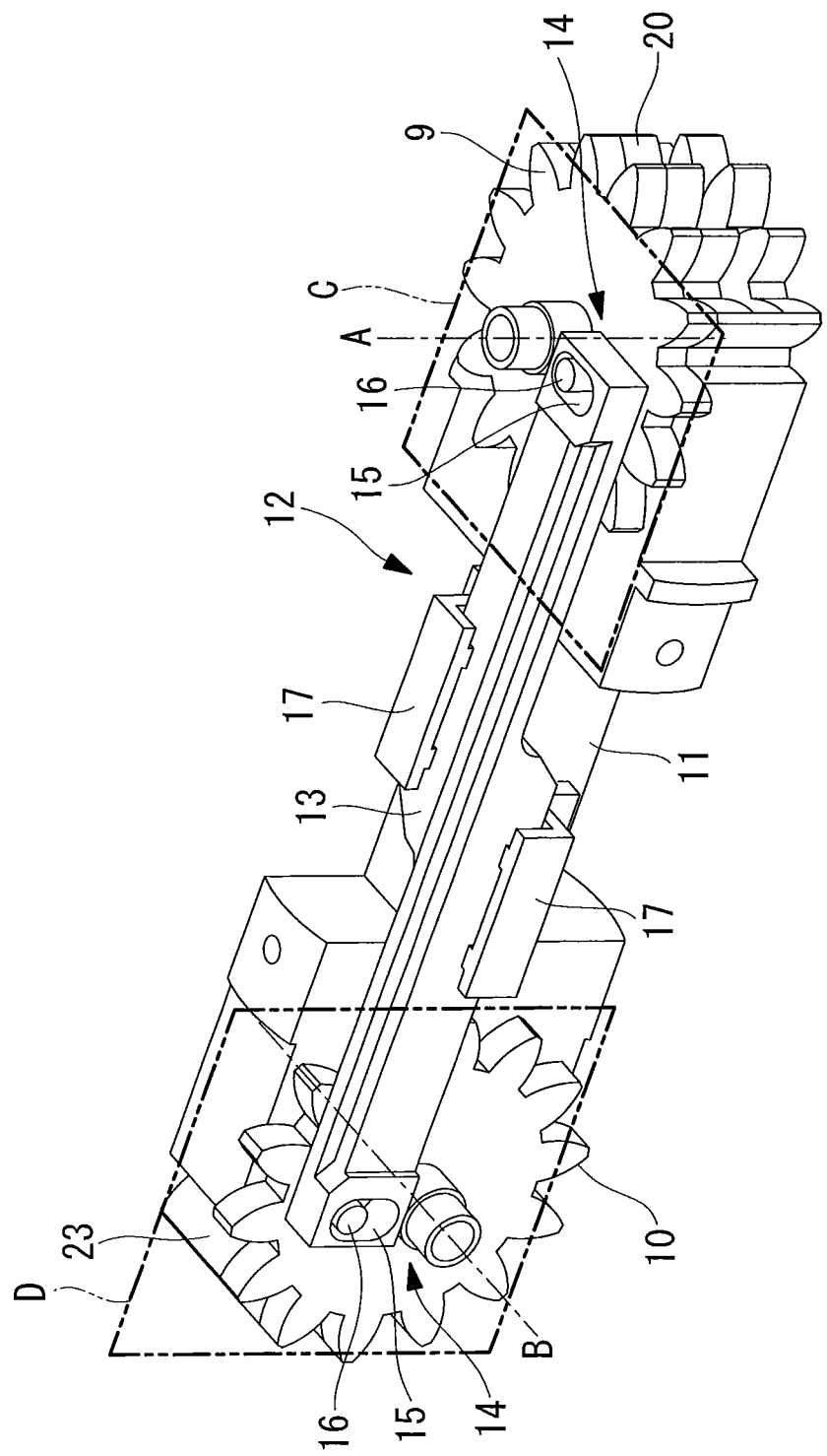
FIG. 2 is a detailed view of a joint mechanism according to the embodiment of the present invention.

As shown in FIG. 2, the joint mechanism 1 according to this embodiment is provided with two spur gears (rotation members) 9 and 10, a support member 11 that supports the spur gears 9 and 10 so as to be rotatable about joint shafts A and B that are disposed in a skew-lines positional relationship with a space between each other, and a rotational-force transmitting mechanism 12 that transmits a rotational force between the spur gears 9 and 10.

As shown in FIG. 2, the support member 11 is formed in a rod shape, and is integrally provided with, at both ends thereof, spur-gear portions 20 and 23 that are formed over a substantially 180° angular range about the joint shafts A and B.

As shown in FIG. 2, the rotational-force transmitting mechanism 12 is provided with a rod-like transmission member 13 that is formed of a rigid piece that is supported in a linearly movable manner, and cam mechanisms 14 that convert the linear motion of the transmission member 13 to the rotational motions of the spur gears 9 and 10 and vice versa.

Figure 3A:
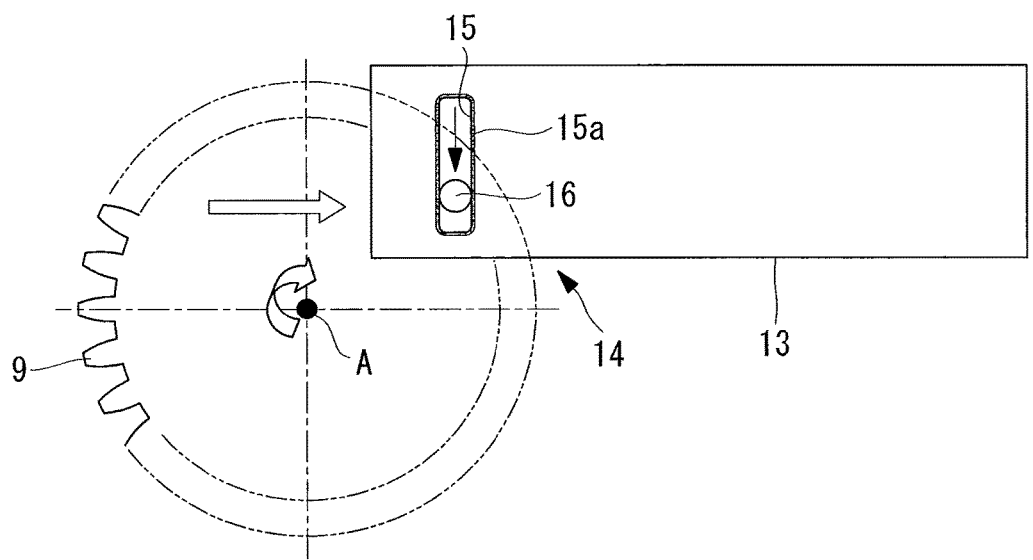
FIG. 3A is an enlarged view of a cam mechanism in the case in which a spur gear on the base-end side of the joint mechanism according to the embodiment of the present invention is rotated clockwise.
Figure 3B:
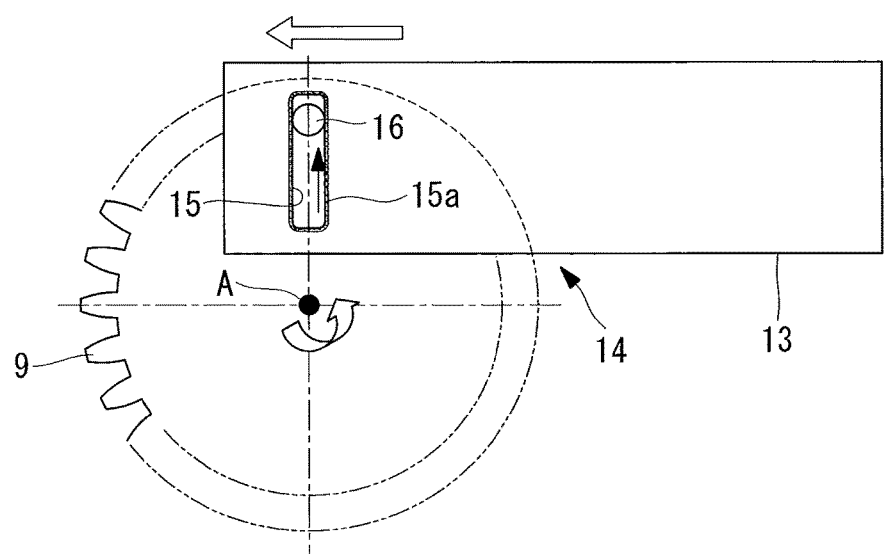
FIG. 3B is an enlarged view of the cam mechanism in the case in which the spur gear on the base-end side of the joint mechanism according to the embodiment of the present invention is rotated anticlockwise.

As shown in FIG. 2, 3A, or 3B, the cam mechanisms 14 are provided with elongated holes 15 that are provided at both ends of the transmission member 13 and that extend in the direction orthogonal to the direction in which the transmission member 13 moves, and pins (movable portions) 16 that are secured to the respective spur gears 9 and 10 so as to be parallel to the joint shafts A and B and that are accommodated in the elongated holes 15 so as to be movable in the longitudinal direction.

As shown in FIG. 2, the transmission member 13 is supported by guide members 17, which are provided in the support member 11, so as to achieve a steady linear motion. The guide members 17 support the transmission member 13 so that the transmission member 13 undergoes a linear motion in a direction parallel to a line of intersection between planes that are orthogonal to the two joint shafts A and B, respectively.

Specifically, in the rotational-force transmitting mechanism 12, when the spur gear 9 is rotated about the joint shaft A, the pin 16, which is secured to the spur gear 9, is also made to undergo rotational motion. The arc motion of the pin 16 includes a component in the direction in which the transmission member 13, which is supported by the guide members 17 so as to be linearly movable in one direction, moves and a component in the direction orthogonal to the direction in which the transmission member 13 moves.

At the cam mechanism 14 on the base-end side, the pin 16 pushes an inner side surface 15a of the elongated hole 15, thus directly transmitting the component in the direction in which the transmission member 13 moves via the linear movement of the transmission member 13, and the component in the direction orthogonal to the direction in which the transmission member 13 moves causes the pin 16 to relatively move in the elongated hole 15, thus escaping without being transmitted to the transmission member 13. By doing so, the rotational motion of the spur gear 9 is converted to the linear motion of the transmission member 13.

At the cam mechanism 14 on the distal-end side, the linear movement of the transmission member 13 causes the elongated hole 15 provided in the transmission member 13 to linearly move. The pin 16 accommodated in the elongated hole 15 is moved by being pushed by the inner side surface 15a of the elongated hole 15. Because the pin 16 is secured to the spur gear 10, which is supported so as to be rotatable about the joint shaft B being in the skew-lines positional relationship with the joint shaft A, the pin 16 is made to undergo a rotational motion that has a component in the direction in which the transmission member 13 moves, the amount of which is the same as the amount by which the transmission member 13 moves. As for the component orthogonal to the direction in which the transmission member 13 moves, this component is allowed to escape due to the relative movement of the pin 16 in the elongated hole 15. By doing so, the linear motion of the transmission member 13 is converted to the rotational motion of the spur gear 10, and thus, it is possible to transmit the rotational motion of the spur gear 9 about the joint shaft A in the form of the rotational motion of the spur gear 10 about the joint shaft B that is in the skew-lines positional relationship with the joint shaft A.

The linkage member 5 on the base-end side is provided with two driving spur gears 18 and 19 that are supported so as to be rotatable about axes that are parallel to the joint shaft A of the spur gear 9. The first driving spur gear 18 is engaged with a spur-gear portion 20 provided at the support member 11 of the joint mechanism 1. The second driving spur gear 19 is engaged with the spur gear 9 that is supported by the support member 11 of the joint mechanism 1 in a rotatable manner. These driving spur gears 18 and 19 are coupled with the drive unit 7 via a transmitting mechanism (not shown) to be individually rotationally driven.

When the first driving spur gear 18 is rotated by operating the drive unit 7, the spur-gear portion 20 engaged with the driving spur gear 18 is rotated about the joint shaft A, and, consequently, the portion on the distal-end side between the support member 11 at which the spur-gear portion 20 is provided and the end effector 3 is pivoted about the joint shaft A.

When the second driving spur gear 19 is rotated by operating the drive unit 7, the spur gear 9 engaged with the driving spur gear 19 is rotated about the joint shaft A.

The linkage member 4 on the distal-end side is provided with a spur-gear portion 21 and a spur gear 22 that are formed at the base-end side of the linkage member 4 over a substantially 180° angular range about axes parallel to the joint shaft B. The spur-gear portion 21 is engaged with a spur-gear portion 23 provided at the support member 11 of the joint mechanism 1. In addition, the spur gear 22 is engaged with the spur gear 10 supported by the shaft portion of the joint mechanism 1.

When the spur gear 10 is rotationally driven, the spur gear 22 engaged with the spur gear 10 is rotated about the joint shaft B, and, consequently, the portion on the distal-end side between the linkage member 4 and the end effector 3 is pivoted about the joint shaft B.

Because the joint shafts A and B are disposed in the skew-lines positional relationship with each other, the support member 11 of the joint mechanism 1 is pivoted about the joint shaft A with respect to the linkage member 4, the linkage member 5 is pivoted about the joint shaft B with respect to the support member 11 of the joint mechanism 1, and thus, the end effector 3 disposed at the distal end of the linkage member 5 is three-dimensionally moved.

The operation of the thus-configured joint mechanism 1 and medical equipment 2 according to this embodiment will be described below.

In order to treat an affected site inside the body of the patient P by using the medical equipment 2 according to this embodiment, as shown in FIG. 1, the end effector 3 provided at the distal-end of the medical equipment 2 is inserted into the body via a through-hole formed so as to pass through the body wall of the patient P, and the control portion 8 is operated.

Figure 4:
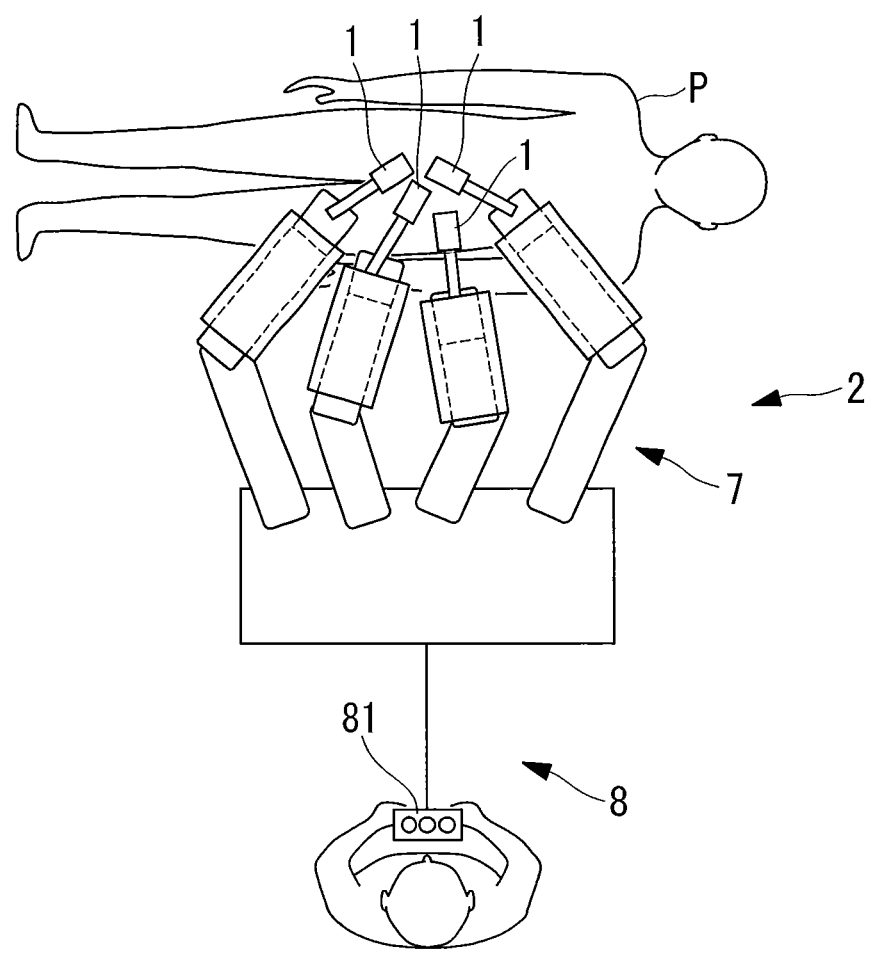
FIG. 4 is an overall configuration diagram of medical equipment employing the joint mechanism according to the embodiment of the present invention.

As shown in FIG. 4, with the medical equipment 2, a user drives the drive unit 7 by means of the control portion 8 via the manipulation portion 81 and places and operates the end effector 3 at a desired position inside the body of the patient P, thus making it possible to treat the affected site.

In this case, with the joint mechanism 1 according to this embodiment, in order to pivot the support member 11 with respect to the linkage member 5, the drive unit 7 is operated by means of signals from the control portion 8 to rotate the driving spur gear 18, thus rotating the spur-gear portion 20 of the support member 11. By doing so, with respect to the linkage member 5, the support member 11 is pivoted about the joint shaft A along a pivoting plane C that is orthogonal to the joint shaft A. On the other hand, in order to pivot the linkage member 4 with respect to the support member 11, the drive unit 7 is operated by means of the signals from the control portion 8, thus rotating the driving spur gear 19 provided at the linkage member 5 on the base-end side.

The rotation of the driving spur gear 19 is transmitted to the spur gear 9 engaged with the driving spur gear 19 in the form of rotation about the joint shaft A. When the spur gear 9 is rotated, due to the operation of the rotational-force transmitting mechanism 12, the rotational motion of the spur gear 9 is converted to the linear motion of the transmission member 13 by the cam mechanism 14 on the base-end side. Then, while the linear motion of the transmission member 13 is supported by means of the guide members 17 so as to keep the linear motion steady, the linear motion is transmitted to the cam mechanism 14 on the distal-end side, and the linear motion transmitted to the cam mechanism 14 on the distal-end side is converted to the rotational motion of the spur gear 10. Specifically, the rotational motion of the spur gear 9 about the joint shaft A is transmitted in the form of the rotational motion of the spur gear 10 about the joint shaft B disposed at the skew-lines position.

When the spur gear 10 is rotated about the joint shaft B, the spur gear 22 engaged with the spur gear 10 is rotated about the joint shaft B, and, consequently, the linkage member 4, which is secured to the spur gear 22, is pivoted about the joint shaft B along a pivoting plane D orthogonal to the joint shaft B.

As a result, the pivoting plane C about the joint shaft A for the support member 11 with respect to the linkage member 5, which is disposed closer to the base-end side than the support member 11 is, is made non-parallel to the pivoting plane D for the linkage member 4, which is connected to the spur gear 10 disposed closer to the distal-end side than the support member 11 is, with respect to the support member 11. Therefore, by combining pivoting along different pivoting planes C and D, it is possible to three-dimensionally move the end effector 3 coupled to the distal end of the linkage member 4, which is on the distal-end side, with respect to the linkage member 5, which is on the base-end side.

In this case, the rotational motion of the spur gear 9 is reliably transmitted by the transmission member 13 formed of the two cam mechanisms 14 and the rigid piece in the form of the rotational motion of the spur gear 10. Therefore, even if a high load is exerted on the linkage member 4 that is closer to the distal-end side than the support member 11 is, it is possible to transmit the high-load rotational force between the two spur gears 9 and 10 that are disposed so as to be rotatable about axes disposed in the skew-lines positional relationship, thus making it possible to endure that load and to move the end effector 3 in a precise manner.

The linear motion of the transmission member 13 is steadily supported by the guide members 17, and thus, it is possible to operate the two cam mechanisms 14 in a highly precise manner.

Figure 5:
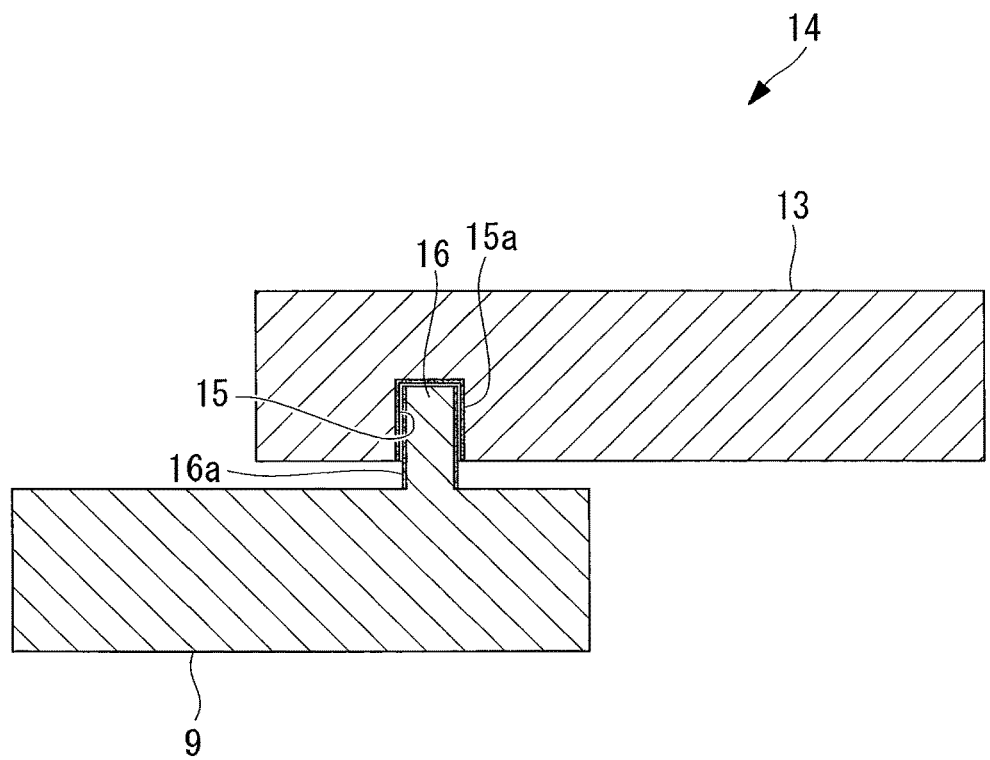
FIG. 5 is an enlarged lateral sectional view of a cam mechanism according to a first modification of the embodiment of the present invention.

In the above-described embodiment, as shown in FIG. 5, with the joint mechanism 1, at least one of the inner side surfaces 15a of the elongated holes 15 and the side surfaces 16a of the pins 16 that come into contact with the inner side surfaces 15a may be formed of a friction-reducing material (for example, polytetrafluoroethylene (PTFE), white metal, or brass).

By doing so, when forces are transmitted between the spur gears 9 and 10 and the transmission member 13, even if the pins 16 and the elongated holes 15 are relatively moved, friction generated between the two is reduced, and thus, it is possible to efficiently transmit the forces.

Figure 6:
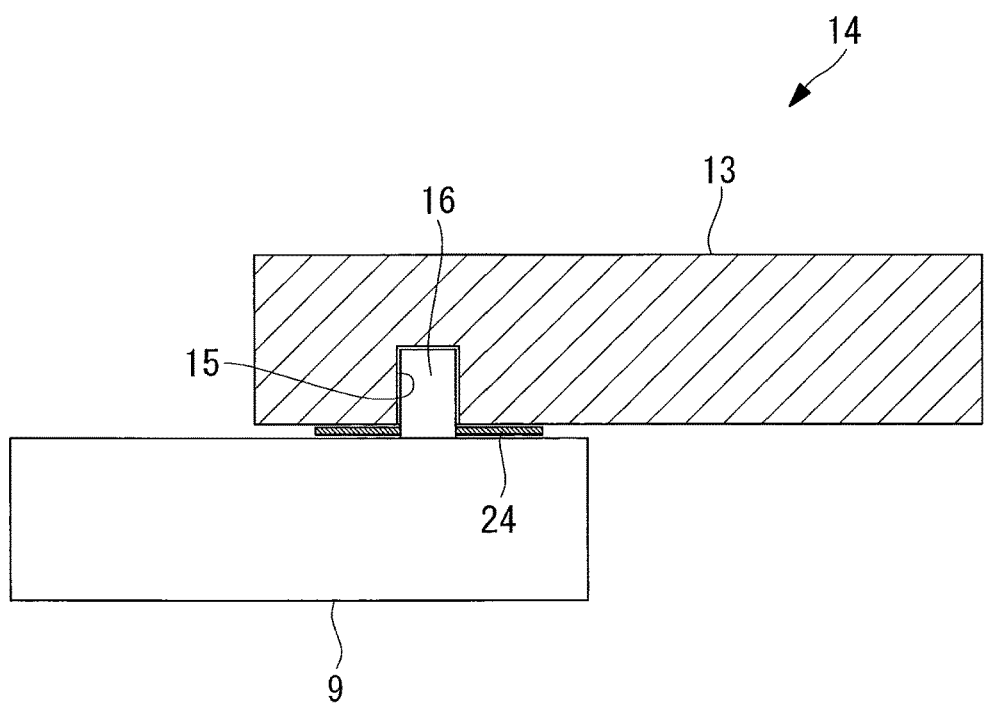
FIG. 6 is an enlarged lateral sectional view of a cam mechanism according to a second modification of the embodiment of the present invention.

In the above-described embodiment, as shown in FIG. 6, with the joint mechanism 1, the cam mechanisms 14 may be provided with low-friction members 24 that are supported by the pins 16, that are interposed between the spur gears 9 and 10 and the transmission member 13, and that are formed of a material (for example, polytetrafluoroethylene (PTFE), white metal, or brass) having a lower coefficient of friction than that of the spur gears 9 and 10 and the pins 16.

By doing so, in association with the rotational motions of the spur gears 9 and 10, frictional forces generated when the transmission member 13 comes into contact with the spur gears 9 and 10 are reduced by having the low-friction members 24 interposed therebetween. Accordingly, the load due to the frictional forces generated when the cam mechanisms 14 convert the rotational motions and the linear motions is reduced, and thus, it is possible to further reduce the load exerted on the joint mechanism 1.

In the above-described joint mechanism 1, the movable portions of the cam mechanisms 14 need not necessarily be formed of the pins 16, and, alternatively, the movable portions may be protrusions that extend from the spur gears 9 and 10 so as to be parallel to the joint shafts A and B.

In the above-described cam mechanisms 14, the elongated holes 15 may be formed so as to pass through the transmission member 13, as shown in FIGS. 2, 3A, and 3B, but the elongated holes 15 need not pass therethrough, as shown in FIGS. 5 and 6.

In this embodiment, as a configuration for decreasing the friction between the transmission member 13 and the spur gears 9 and 10, the pins 16 may be supported by bearings instead of employing the low-friction members 24.

Although the cam mechanisms 14 formed of the elongated holes 15 and the pins 16 have been described as examples in this embodiment, there is no limitation thereto, so long as the rotational motion and the linear motion can be converted at connecting portions between the spur gears 9 and 10 and the transmission member 13. To serve as the cam mechanisms 14, it suffices that the elongated holes 15 be provided in one of the spur gears 9 and 10 and the transmission member 13 and that the pins 16 be provided at the other of the spur gears 9 and 10 and the transmission member 13.

In the above-described medical equipment 2, the end effector 3 may be an endoscope instead of forceps.

The above-described medical equipment 2 may be additionally provided with, between the joint mechanism 1 and the linkage member 4 on the distal-end side, an additional joint mechanism 1 or another joint mechanism that is configured such that the joint shafts A and B of the spur gears 9 and 10 of the joint mechanism 1 are parallel to each other.

By doing so, it is possible to increase the number of locations to be bent, and it is possible to increase the operating range of the end effector 3 by increasing the pivoting angular range of the end effector 3 with respect to the linkage member 5 on the base-end side.

Figure 7:
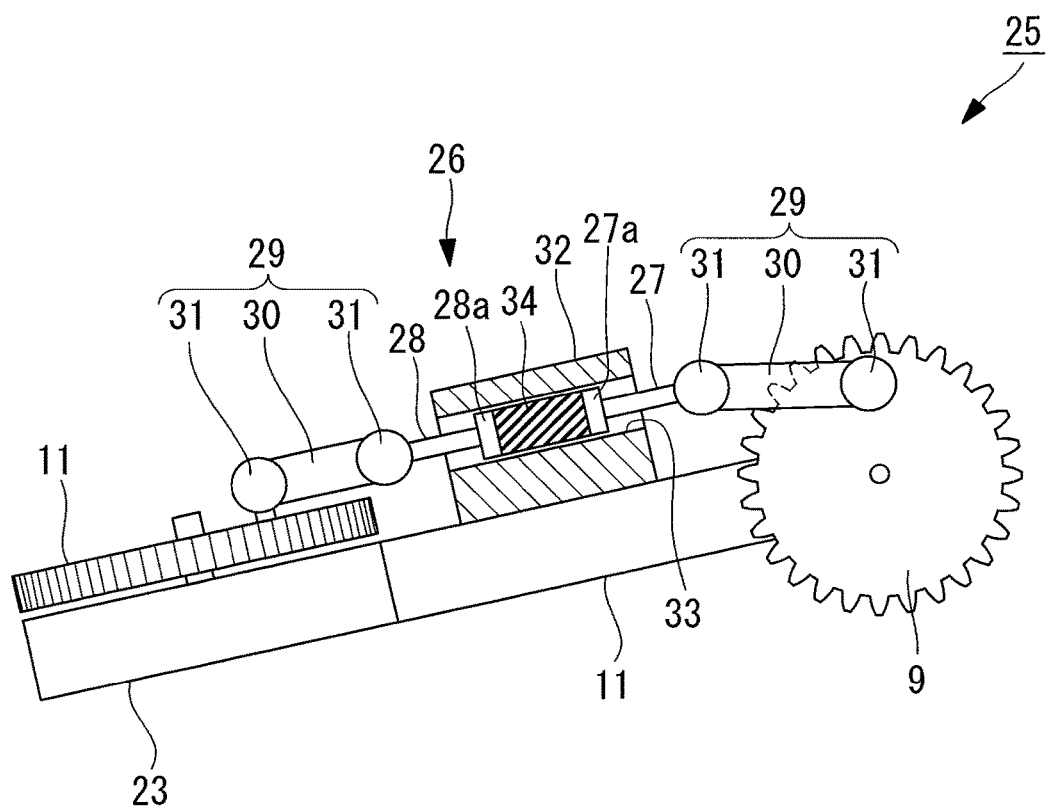
FIG. 7 is a schematic view of a joint mechanism according to a third modification of the embodiment of the present invention.

As shown in FIG. 7, in this embodiment, two pistons 27 and 28 may be employed instead of the above-described transmission member 13, linkage mechanisms 29 may be employed instead of the cam mechanisms 14, and a cylinder member 34 that accommodates the pistons 27 and 28 so as to allow linear movement thereof may be employed as a guide member 32.

The linkage mechanisms 29 are provided with linkage members 30 formed of rigid pieces and two pivoting-shaft portions 31 that attach the two ends of the linkage members 30 to the spur gears 9 and 10 and the pistons 27 and 28 so as to be pivotable about two axes that are parallel to the joint shafts A and B.

An incompressible fluid is sealed between the two pistons 27 and 28 that are accommodated in a through-hole 33 of the cylinder member 34.

By employing such a configuration, when the spur gear 9 is rotated about the joint shaft A, by means of the linkage mechanism 29 attached to the spur gear 9, a component of the rotational motion of the spur gear 9 in the direction orthogonal to a direction in which the piston 27 moves is allowed to escape due to the pivoting of the two ends of the linkage member 30 about axes parallel to the joint shaft A. In addition, a component of the rotational motion of the spur gear 9 in the direction in which the piston 27 moves is converted to the linear motion of the piston 27 by an amount corresponding to the difference between the amounts of displacement at the two ends of the linkage member 30. By doing so, by means of the linkage mechanism 29, it is possible to convert the rotational motion of the spur gear 9 to the linear motion of the piston 27 without causing deflection and deterioration in the members, and it is possible to efficiently transmit the forces.

It is preferable to employ ball joints as the pivoting-shaft portions 31. By doing so, it is possible to more efficiently transmit the forces.

The linear motion from the piston 27 is transmitted to the incompressible fluid inside the guide member 32, and, due to the fluid pressure (for example, hydraulic pressure) of the incompressible fluid, the linear motion is transmitted to the piston 28 in the same amount as the amount by which the piston 27 is moved. By doing so, the linear motion transmitted to the piston 28 is converted to the rotational motion of the spur gear 10. As a result, the two pistons 27 and 28 are supported by the cylinder member 34 in a highly rigid and highly precise manner so as to allow linear movement, and thus, it is possible to more reliably transmit the forces from the spur gear 9 to the spur gear 10.

With the above-described joint mechanism 25, at least one of an inner side surface 33a of the through-hole 33 and side surfaces 27a and 28a of the pistons 27 and 28 that come into contact with the inner side surface 33a may be formed of a friction-reducing material (for example, polytetrafluoroethylene (PTFE), white metal, or brass).

By doing so, even if the pistons 27 and 28 and the through-hole 33 are relatively moved when forces are transmitted between the pistons 27 and 28 and the cylinder member 34, friction generated between the two is reduced, and thus, it is possible to efficiently transmit the forces.

The above-described embodiment is derived from individual aspects of the present invention described below.

An aspect of the present invention is a joint mechanism including two rotation members; a support member that supports the two rotation members so as to be rotatable about two joint shafts that are disposed in a skew-lines positional relationship with a space between each other; and a rotational-force transmitting mechanism that transmits a rotational force between the rotation members, wherein the rotational-force transmitting mechanism is provided with a transmission member formed of a rigid piece that is supported so as to be movable only in a direction parallel to a line of intersection between planes that are respectively orthogonal to the two joint shafts and cam mechanisms or linkage mechanisms that are disposed between the transmission member and the two rotation members, respectively, and that convert rotational motions of the rotation members to a linear motion of the transmission member.

With this aspect, when the rotational force about the first joint shaft is applied to the first rotation member supported by the support member in a rotatable manner, due to the operation of the rotational-force transmitting mechanism, the rotational motion of the rotation member is converted to the linear motion of the transmission member by the first cam mechanism or linkage mechanism. Furthermore, the second cam mechanism or linkage mechanism converts the linear motion of the transmission member to the rotational motion of the second rotation member. Specifically, the rotational motion of the first rotation member about the first joint shaft is transmitted in the form of the rotational motion of the second rotation member about the second joint shaft that is disposed in the skew-lines positional relationship. As a result, the pivoting plane of the support member about the first joint shaft with respect to the member disposed closer to the base-end side than the support member is and the pivoting plane of, with respect to the support member, the member connected to the second rotation member disposed closer to the distal-end side than the support member is can be set to be non-parallel, and, by combining bending about the two joint shafts, it is possible to three-dimensionally move the distal end of the member on the distal-end side with respect to the member on the base-end side.

In this case, the rotational motion of the first rotation member is reliably transmitted in the form of the rotational motion of the second rotation member by the transmission member formed of the two cam mechanisms or linkage mechanisms and the rigid piece. Therefore, even if a high load is exerted on the member closer to the distal-end side than the support member is, the high-load rotational force is transmitted between the two rotation members disposed so as to be rotatable about the axes that are disposed in the skew-lines positional relationship, which makes it possible to endure the high load, and thus, it is possible to precisely move the member on the distal-end side.

In the above-described aspect, the support member may be provided with a guide member that supports the transmission member so as to allow linear movement thereof.

By doing so, the linear motion of the transmission member is steadily supported by the guide member, and thus, it is possible to operate the two cam mechanisms or linkage mechanisms in a highly precise manner.

In the above-described aspect, the cam mechanism may include a elongated hole that is provided in one of the rotation member and the transmission member and that extends in a direction that intersects a direction in which the transmission member moves and a movable portion that is accommodated in the elongated hole so as to be movable in the elongated hole in a longitudinal direction and that is provided in the other of the rotation member and the transmission member.

By doing so, when the first rotation member is rotated, the elongated hole or the movable portion provided in this rotation member undergoes an arc motion together with the rotation member. Of the rotational force due to the arc motion, a force component in the direction in which the transmission member moves is transmitted from the rotation member to the transmission member by abutting the movable portion against the inner side surface of the elongated hole. On the other hand, a force component in the direction that intersects the direction in which the transmission member moves is allowed to escape by moving the movable portion in the longitudinal direction of the elongated hole. By doing so, it is possible to convert the rotational motion of the first rotation member to the linear motion of the transmission member in a simple manner.

In addition, when the transmission member is made to undergo a linear motion, the elongated hole or the movable portion provided in the transmission member is made to undergo a linear motion together with the transmission member. The pressing force due the linear motion is transmitted from the transmission member to the second rotation member by abutting the movable portion against the inner side surface of the elongated hole. The arc motion of the second rotation member is tolerated by moving the movable portion in the longitudinal direction of the elongated hole. Accordingly, it is possible to convert the linear motion of the transmission member to the rotational motion of the second rotation member in a simple manner.

In the above-described aspect, at least one of an inner side surface of the elongated hole and a side surface of the movable portion that comes into contact with the inner side surface may be formed of a friction-reducing material.

By doing so, when forces are transmitted between the rotation member and the transmission member, even if the movable portion and the elongated hole are relatively moved, friction generated between the two is reduced and thus, it is possible to efficiently transmit the forces.

In the above-described aspect, the linkage mechanism may be provided with a linkage member and two pivoting-shaft portions that attach two ends of the linkage member to the rotation member and the transmission member so as to be pivotable about two axes that are parallel to the joint shaft.

By doing so, when the rotation member is rotated about the joint shaft, the linkage member that is coupled so as to be pivotable about the axes that are parallel to the joint shaft is pivoted with respect to the rotation member and the transmission member, and the rotational motion of the rotation member is converted to the linear motion of the transmission member. In this case, it is possible to convert the rotational motion to the linear motion by means of the linkage mechanism without causing deflection and deterioration in the members, and thus, it is possible to efficiently transmit the forces.

In the above-described aspect, the transmission member may be formed of two pistons, and the guide member may be formed of a member that accommodates the two pistons so as to allow linear motions thereof and that has a through-hole in which an incompressible fluid can be sealed between the pistons.

By doing so, the two pistons are supported by the cylinder member in a highly rigid and highly precise manner so as to allow linear motions thereof, and thus, it is possible to more reliably transmit forces from the first rotation member to the second rotation member.

Another aspect of the present invention may provide medical equipment including a first linkage having an end effector at a distal end thereof; a second linkage; and a joint mechanism that couples the first and second linkages by employing any one of the joint mechanisms according to the individual aspects described above.

In this aspect, when the two linkages are coupled to the joint mechanism, because the pivoting plane of the first linkage with respect to the support member and the pivoting plane of the second linkage with respect to the support member are in the skew-lines positional relationship, by combining bending about the two joint shafts, it is possible to three-dimensionally move the end effector with respect to the second linkage. By doing so, even in a location where it is difficult to perform medical treatment, such as the body interior or the like of an animal or a person, it is possible to place the end effector in a desired position and direction, thus easily performing treatment and observation.

REFERENCE SIGNS LIST 1, 25 joint mechanism
2 medical equipment
3 end effector
4, 5 linkage member
9, 10, 22 spur gear (rotation member)
11 support member
12, 26 rotational-force transmitting mechanism
13 transmission member
14 cam mechanism
15 elongated hole
16 pin (movable portion)
17, 32 guide member
27, 28 piston (transmission member)
29 linkage mechanism
30 linkage member
31 pivoting-shaft portion
33 through-hole
34 cylinder member

The invention claimed is:

1. A joint mechanism comprising:
two rotation members;
a support member that supports the two rotation members so as to be rotatable about two joint shafts that are disposed in a skew-lines positional relationship with a space between each other; and
a rotational-force transmitting mechanism that transmits a rotational force between the two rotation members,
wherein the rotational-force transmitting mechanism is provided with a transmission member and cam mechanisms,
the transmission member is formed of a rigid piece that is supported so as to be movable only in a direction parallel to a line of intersection between planes that are respectively orthogonal to the two joint shafts,
the cam mechanisms are disposed between the transmission member and the two rotation members, respectively, and convert rotational motions of the two rotation members to a linear motion of the transmission member, and
each of the cam mechanisms includes an elongated hole that is provided in one of the transmission member and a corresponding rotation member of the two rotation members, each elongated hole extends in a direction that intersects a direction in which the transmission member moves, each cam mechanism includes a movable portion that is accommodated in the elongated hole so as to be movable in the elongated hole in a longitudinal direction, the movable portion being provided in the other of the transmission member and the corresponding rotation member of the two rotation members.

2. A joint mechanism according to claim 1, wherein the support member is provided with a guide member that supports the transmission member so as to allow linear movement thereof.

3. A joint mechanism according to claim 1, wherein at least one of an inner side surface of the elongated hole and a side surface of the movable portion that comes into contact with the inner side surface is formed of a friction-reducing material.

4. A medical equipment comprising:
a first linkage having an end effector at a distal end thereof;
a second linkage; and
a joint mechanism according to claim 1, which couples the first and second linkages.

* * * * *